(12) United States Patent
Kuth

(10) Patent No.: US 7,181,263 B2
(45) Date of Patent: Feb. 20, 2007

(54) INJECTION SYSTEM FOR USE IN A MEDICAL IMAGING EXAMINATION

(75) Inventor: Rainer Kuth, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 607 days.

(21) Appl. No.: 10/456,071

(22) Filed: Jun. 6, 2003

(65) Prior Publication Data
US 2004/0068176 A1    Apr. 8, 2004

(30) Foreign Application Priority Data
Jun. 6, 2002  (DE)  ................. 102 25 223
Jan. 23, 2003  (DE)  ................. 103 02 636

(51) Int. Cl.
*A61B 5/05*    (2006.01)
(52) U.S. Cl. ...................... 600/420; 407/431
(58) Field of Classification Search ................. 600/432, 600/431
See application file for complete search history.

(56) References Cited

U.S. PATENT DOCUMENTS 4,006,736 A * 2/1977 Kranys et al. .............. 600/432
4,921,480 A * 5/1990 Sealfon ....................... 604/65
5,269,762 A   12/1993 Armbruster et al.
5,322,511 A    6/1994 Armbruster et al.
5,935,111 A    8/1999 Bunyan

FOREIGN PATENT DOCUMENTS

| DE | 1 566 585 | 7/1970 |
| DE | 34 19 347 | 12/1987 |
| DE | 41 23 441 | 1/1992 |
| DE | 196 47 701 | 5/1998 |

* cited by examiner

*Primary Examiner*—Brian L. Casler
*Assistant Examiner*—James Kish
(74) *Attorney, Agent, or Firm*—Schiff Hardin LLP

(57) ABSTRACT

An injection system for medical examinations to control the manual injection of a substance into a patient with a manually operated injector that has an arrangement to detect the fill state of a container filled with a substance to be injected. To detect the fill state, the volume occupied by the substance can be directly measured, can be indirectly determined by measuring the position of a component of the injection device that is correlated to the occupied volume.

12 Claims, 3 Drawing Sheets

INJECTION SYSTEM FOR USE IN A MEDICAL IMAGING EXAMINATION

BACKGROUND OF THE INVENTION

1. Field of the Invention

The present invention concerns an injection system for medical imaging examinations with a manually operated injector.

2. Description of the Prior Art

In medical imaging examinations, contrast agents dissolved in liquid often are administered. These injections, which are known as bolus injections, enable a more marked contrast in the imaging of tissues with the examination device. Given a temporally well-defined bolus injection as well as improvement of the contrast, details can be derived from the temporal progression with which the contrast agent spreads out in the tissue, for example, about disturbances in the blood-tissue barriers,. The temporal coordination, i.e. the timing of the bolus injection and the start of the measurements with the radiological examination device, is fundamental for reproducibility and high quality in this technology. In the majority of cases, the bolus injection is done manually with a syringe by the doctor. The point in time of the injection is then communicated by a verbal notification to the operator of the radiological examination device. In addition, automated injectors are known which are controlled via a terminal. These have the disadvantage that complications may become apparent too slowly, since the automatic bolus injections generally are not directly monitored. Complications that can occur during an injection are, for example, a leak or tear in the injection tube.

A device for contrast density regulation is known from German OS 19 647 701. The device comprises a sensor that is connected to a processing unit. The sensor can determine the concentration of contrast agent or the contrast density in individual areas of the body. A comparison of measured and rated values is converted into a control pulse that is transmitted to a pump system.

German PS 3 419 347 shows a device to continually output a disinfected, sterile, physiological liquid that, given increasing depletion, exerts a consistent pressure on the liquid.

An injection device for x-ray contrast agent is described in German OS 1 566 585 that has a constant injection output that is independent of geometry, viscosity, and flow resistance of the injected substance.

A device for determining the concentration of at least one substance present in an organic tissue with a pump-and-suction device controlled by a microprocessor is disclosed in German OS 4 123 441.

SUMMARY OF THE INVENTION

An object of the present invention is to provide an injection system with a manually operated injector that improves temporal coordination of a bolus injection with the start of a measurement with a radiological examination device.

This object is achieved in accordance with the invention in an injection system for medical imaging examinations with a manually operated injector to control manual injections of a substance into a patient, having an arrangement for detecting the fill state of a container containing the substance to be injected, and providing an indication dependent on the fill state. This allows a reliable synchronization-independent of verbal communication—of, for example, an imaging examination (assisted by a contrast agent dissolved in a liquid) with the fill state of the container. A signal can thus be generated, for example at a specific point in time, when the arrangement detects that the container is still occupied by the substance, or no longer occupied. The invention enables a form of controlled manual injection, in which the time curve of the delivery of the substance to be injected is recorded. The substance to be injected can be, for example, a contrast agent or a drug.

In an embodiment of the injection system the arrangement for the detection of the fill state detects a point (position) that a component of the injector passes through during emptying of the reservoir. This has the advantage that, for example, only the motion of a component through one or more points must be monitored, independent of the speed of emptying. The motion of the component is associated with the emptying of the container. For example, the component can directly effect the emptying, or can be structurally connected to a component that effects the emptying, such that the motions of both components are correlated.

In a preferred embodiment of the injection system the detector arrangement is formed by a chamber in fluid communication with the container. Due to the injection procedure, the substance to be injected temporarily occupies a volume in the chamber that serves as the indication of the fill state. This has the advantage that the imaging examination device effecting the examination can be employed to determine the volume that is momentarily occupied. This has the further advantage that the information about the fill state is directly available in the imaging, for example in a magnetic resonance acquisition.

In a preferred development, the chamber encloses a marking volume that has a connection with a supply line that directs the substance from the injector to the patient. The fill state of the marking volume can be dependent on pressure exerted on the substance.

The separation of the chamber from the injector has the advantage that each can be positioned independently of one another. The pressure exerted on the substance during the injection determines the fill state of the marking volume in the chamber. The fill state correlates in this way to the injection procedure, such that the detection of the fill state enables an improved temporal coordination of an injection with the start of a measurement by an imaging examination device.

In a version of this embodiment, the chamber has a marker formed by a marking volume filled with the substance to be injected, and a gas receiver, the marking volume being separated from the gas reservoir by a pressure-reactive membrane. The gas reservoir serves as an equalization volume that allows a change of the fill state in the marking volume, as well as providing a clarification for the evaluation of the fill state by increasing the contrast between the substance and gas in the imaging (if the imaging device is used for that purpose).

In a further embodiment, the marker is arranged in the imaging region of a device conducting the examination (in particular a computed tomography or magnetic resonance device) so that a change is detectable by the examination device as to the fill state of the marking volume filled with the substance to be injected. The imaging region may change, so that it can be advantageous to use multiple markers in order make use of all forms if the imaging region, or it may be more favorable to re-position the markers with the changed image region.

In a further embodiment, the arrangement to detect the fill state is able to detect a number of different fill states in order to detect the time curve of the injection, in particular the beginning and/or end of the injection. For example, the duration of the injection procedure can be determined from the time curve.

In another embodiment, the container is a reservoir of the injector. This has the advantage that the arrangement to detect the fill state can be constructed as a unit with the injector.

In an embodiment, the injector is formed as a piston pump. An example of a piston pump is, for example, a syringe needle.

In a further advantageous embodiment, the arrangement to detect the fill state has a switch that recognizes departure from an initial fill state or the occurrence of an ending (final) fill state.

The switch can have an actuator disposed at an initial position occupied by the piston at a beginning of the injection and/or an actuator disposed at a final position occupied by the piston at the end of the injection.

The arrangement to detect the fill state can have a timing element to evaluate the time curve of the injection, in particular to measure the time between the beginning and the end of the injection. This allows an evaluation of the time curve of the injection and has the advantage of making the different points in time and time intervals of the injection procedure such as, for example, the time interval between beginning and end of the injection, available as electronic information.

The arrangement to detect the fill state can have fiber-optic and/or magnetic and/or pneumatic and/or pneumatic-dynamic switches. Such switches can be formed so that they can be robustly and easily sterilized or decontaminated (autoclaved), as is appropriate for the injection system in clinical everyday use. Furthermore, they require no electrical cables or ferromagnetic components that can produce noise in the images in the radiological examination. An exception is the magnetic switch that cannot be used in a magnetic resonance device, or used only outside of the imaging region. Additionally, it is beneficial to use switches or sensors in the acquisition region that function without local energy supplies. This is the case with switches that are based on pneumatic or hydraulic principles.

In a preferred embodiment, the arrangement detecting the fill state has a signal output for control data, in particular for control of an imaging examination device. For example, information about the injection procedure (start and end times, duration) that can be directly transmitted to an examination device is available at the signal output.

In another embodiment, the arrangement to detect the fill state transmits information to a control unit about the administration of the injected substance. This enables a warning signal to be emitted, for example in the event of a deviation from the standard sequence of the time curve of an injection.

A further use of the injection system is for multiple injections of, for example, identical or different drugs, with which an improved effect can be achieved. The temporal coordination of the injections ensues by means of the control unit and special timing elements.

In an embodiment, the injection system is used together with an imaging examination device, in particular with a magnetic resonance tomography device.

DESCRIPTION OF THE PREFERRED EMBODIMENTS

Figure 1:
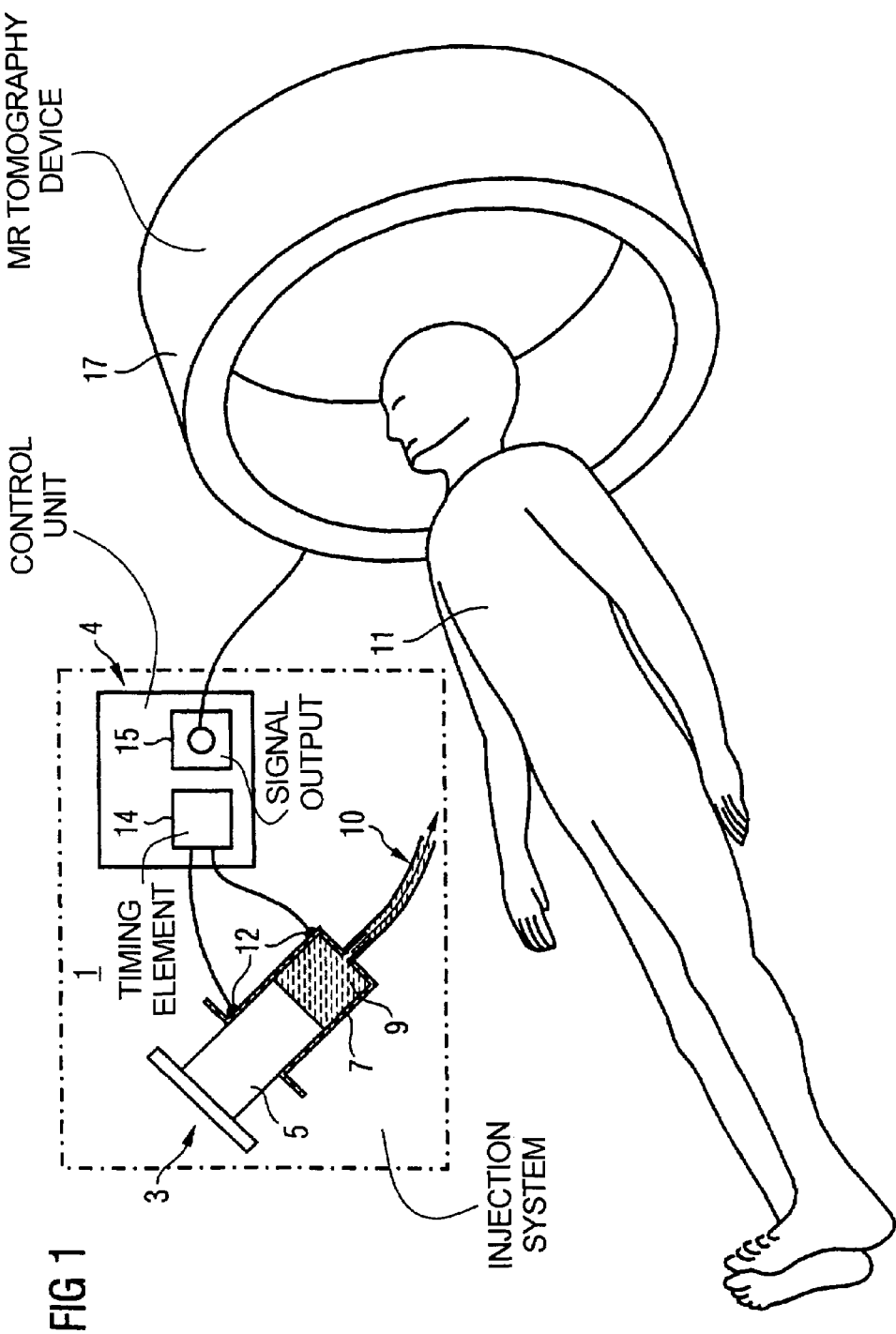
FIG. 1 is an overview of an injection system for an imaging examination with a manually operated injector, including an arrangement for monitoring the injection procedure in one embodiment of the invention.

FIG. 1 shows an injection system 1 for controlled injections of a substance 9, preferably a contrast agent for radiological examinations. It has a manually operated injector 3 and a control unit 4. The injector 3 is composed of a piston 5 and a cylinder 7 in the form of a syringe.

The substance 9 to be injected is disposed in a container (a reservoir in this embodiment) that is formed by the piston 5 and the cylinder 7 of the injector 3. The substance is intravenously injected into the patient 11 via a supply line 10 by moving the piston 5 into the cylinder 7. The position of the piston 5 thus determines the fill state of the reservoir. In the injector 3, a switches 12 are respectively disposed at two points along the cylinder 7. The switches 12 are connected to the control unit 4 and communicate to the control unit 4 that the piston 5 has reached the point and thus that the reservoir is filled. The switches 12 can be, for example, magnetic switches that are activated by a metal ring in the piston 5.

The control unit 4 has a timing element 14 that measures the time interval between the passage of the pistons along two points, and evaluates whether the time interval lies within a tolerance range. If this is the case, the control unit 4 applies a signal to a signal output 15 that indicates the start time of the injection, and that is transmitted to an imaging medical examination device 17.

Figure 2:
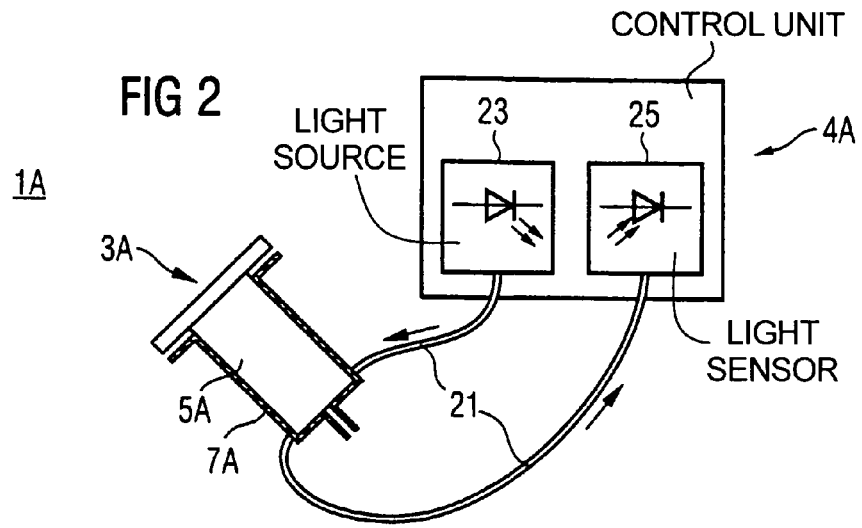
FIG. 2 shows an injector with a fiber-optic switch to determine the end of an injection for use in the inventive system.

An injection system 1A with an injector 3A and a fiber-optic switch that preferably is used with a magnetic resonance device is shown in FIG. 2. The fiber-optic switch includes a light conductor 21, a light source 23, and a light sensor 25. The light from the light source 23 is emitted into the light conductor 21 in the control unit 4A. The light conductor 21 conducts the light to the face at the output of the injector 3A. There, the light traverses, with certain losses the cylinder 7A with the substance to be injected, and is finally conducted from a second part of the light conductor 21 to the light sensor 25, which is likewise located in the control unit 4A. As soon as the piston 5A reaches the end of the cylinder 7A, it blocks the transfer of light to the light sensor 25. This generates an electronic signal in the control unit 4A with the information that the piston 5A has completely filled the reservoir of the injector 3A. This means that no more substance is available and the injection is ended. Further fiber-optic switches can be mounted to monitor further points of the piston 5A in the injector 3A, such that the time-dependent fill state, and thus the course of the injection, can be detected as well.

Figure 3:
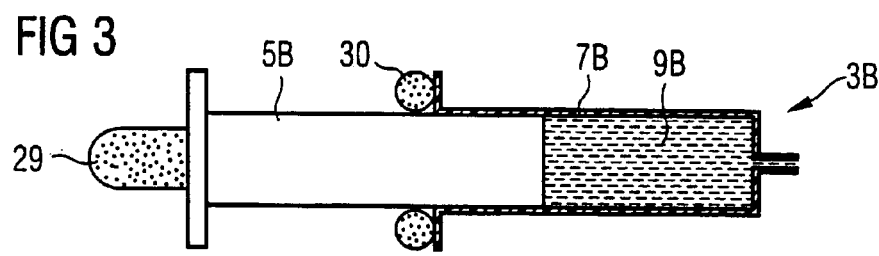
FIGS. 3, 4, and 5 illustrate a further injector having pneumatic-dynamic switches in successive positions during an injection.
Figure 4:
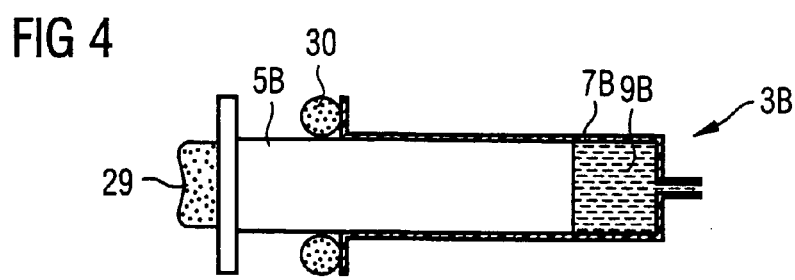
Figure 5:
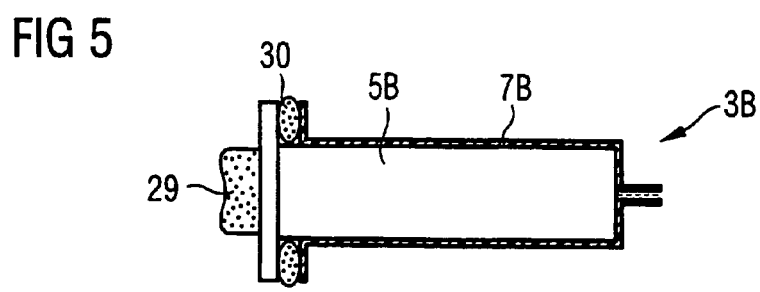

A variant of an injector 3B with a combination of a pneumatic switch and a pneumatic-dynamic switch is shown in FIGS. 3 through 5. These switches each have a gas-filled reservoir 29 or 30 that is subjected to pressure variations during the injection procedure. The pressure variations are measured either statically (pneumatic switches) or dynamically (pneumo-dynamic switches) via gas-filled supply lines. The supply lines to both the pressure-sensitive switch reservoirs 29 and 30 as well as the sensors in the control unit are not drawn.

FIG. 3 illustrates the situation at a point in time shortly after the beginning of the injection. The fill volume of the switch reservoir 29 of the pneumatic-dynamic switch is reduced by the pressure of the thumb during pressure application on the piston 7B. Since the pneumatic-dynamic switch before is in the standby position, the pressure change transmitted to and registered in the control unit signifies that the output fill volume is no longer present and that, consequently, the injection has begun.

The situation at the end of the injection is shown in FIG. 5. Upon the piston 5B reaching the stop position, the pressure in the torus-shaped switch reservoir 30 increases and is transduced into an electrical signal that provides the information that the piston 5B is at the stop position, i.e., no more substance to be injected is present in the reservoir, and thus that the injection is ended.

The intermediate situation is shown in FIG. 4/

Instead of the switch based on the pneumatic mode of operation, hydraulic switches can be used in an easily modified system.

Figure 6:
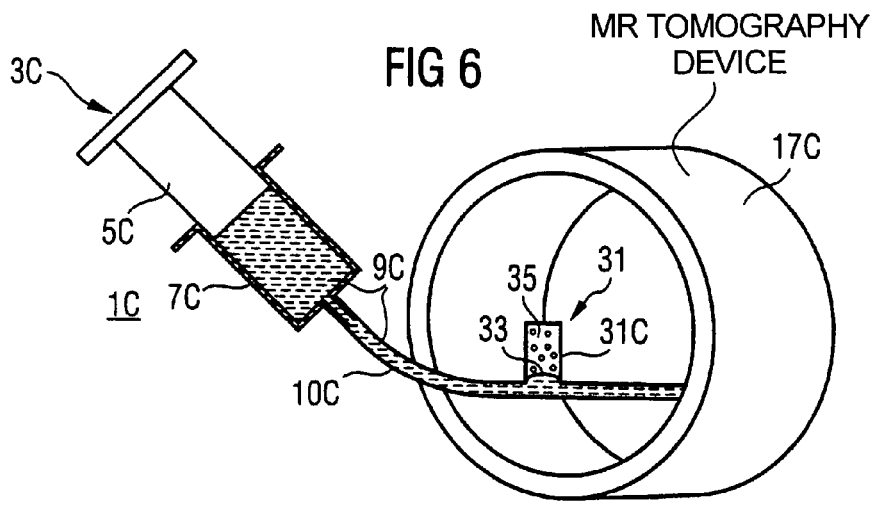
FIGS. 6, 7, and 8 show an alternative embodiment of an inventive injector system with a marker that is located within the imaging region of an examination device.
Figure 7:
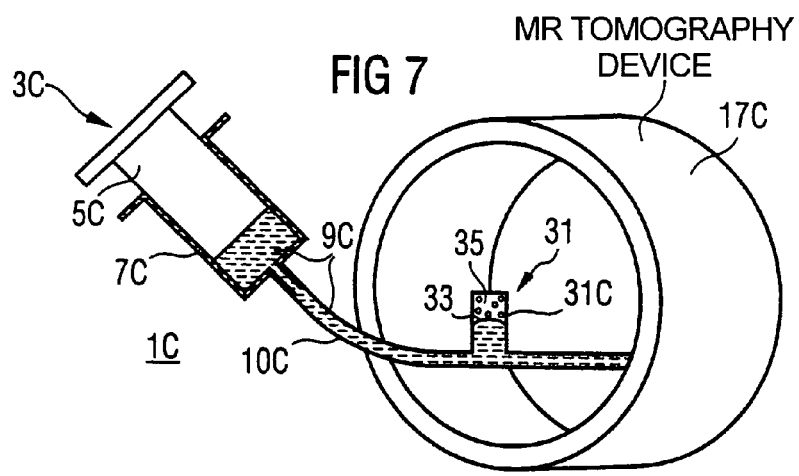
Figure 8:
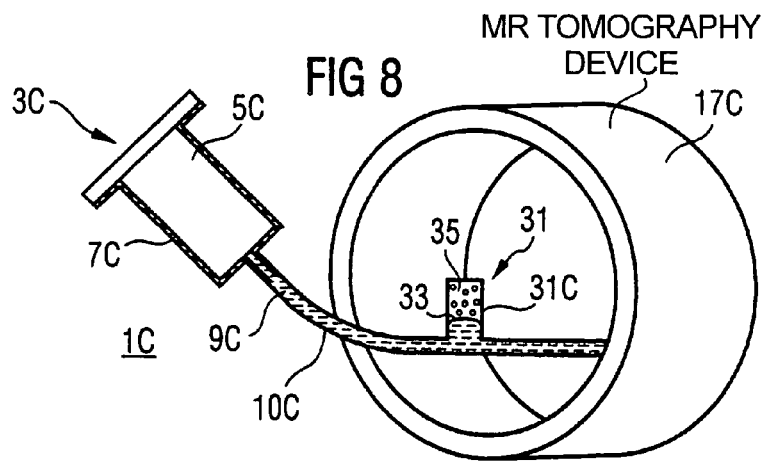

An alternative embodiment of an injection system 1C with a chamber serving as a marker 31 is shown in FIGS. 6 through 8, wherein the marker 31 is arranged inside of the imaging region of an imaging medical examination device 17C, for example a magnetic resonance tomography device. The marker 31 is attached, for example, to the patient bed of the medical examination device 17C, such that is always located in the same known position in different magnetic resonance tomography images.

The marker 31 has a sub-chamber containing a marking volume 31C that is connected to a supply hose 10C and filled with the substance 9C to be injected. The dimensions (volume) of the marking volume 31C are dependent on the pressure that is present in the supply line 10C during the injection procedure. The marker 31 is formed of material either allowing the marking volume 31C to be visually observable and/or detectable by whatever imaging modality is employed.

The marker 31 additionally has another sub-chamber forming a gas reservoir 35 that is separated from the substance 9D to be injected by a pressure-responsive membrane 33. The gas reservoir 35 generates a good contrast around the marking volume 31A, for example, in a magnetic resonance image, and facilitates the evaluation of the fill state. The fill state of the marker 31 also can be determined indirectly from the size of the volume of the gas reservoir 35.

The fill state of the marking volume 31C in the marker 31 before the beginning of the injection is shown in FIG. 6. The gas reservoir 35 occupies the largest portion of the marking volume 31C. Since no pressure is exerted on the substance 10C, the membrane 33 is in the relaxed state.

A snapshot of the injection procedure is shown in FIG. 7. A liquid substance 9C is injected by exerting pressure on the piston 5C, the pressure is transferred to the viscosity, such that an increased pressure is likewise present in the supply line 10C. The membrane 33 yields until the force of the pressure in the compressed gas reservoir 35 and the elasticity due to the stretching of the membrane 33 is at equilibrium with the increased pressure on the substance 9C.

The fill state of the marking volume 31C in the marker after the injection is shown in FIG. 8. Due to the pressure in the container, a light excess pressure is present in the supply line 10C that is again compensated by the counteractive forces in the marker 31. The fill state of the marker 31 with the residual substance 9C in the supply line is somewhat larger than the fill state before the injection.

The stretching, and thus the fill state, can be monitored during operation of the medical examination device 17C, and allow a subsequent evaluation of the temporal connection between injection and acquisition.

Additionally, for example, the portion of the imaging region in which the marker 31 is located can be selectively imaged with the medical examination device. The information about the size of the marking volume 31A, and therewith about the fill state of the marker 31, can automatically simultaneously track the injection by image processing, and be used to control the medical examination device 17C.

Consequently, the injection system 1C presents a versatile variant for the detection of the injection procedure, since the examination device 17C is used to detect and record spatial dimensions and changes of a reservoir filled with the substance 9C to be injected, i.e. for example to correspondingly mark the images obtained with an examination device.

The changes of the fill state in marker 31 alternatively can be measured as well with the above-described switches by, for example, position changes of the membrane being detected instead of position changes of the piston.

In FIGS. 1 through 8, examples of the detection of the fill state of a reservoir filled with substances 9, 9B, and 9C were shown. The volume of the substance 9C occupying volume in the marker 31 can be directly measured, the fill state can be indirectly measured by measuring the position of a component 5, 5A, 5B of the injection device 1, 1a, 1B, whose position correlates to the occupied volume.

Although modifications and changes may be suggested by those skilled in the art, it is the intention of the inventor to embody within the patent warranted hereon all changes and modifications as reasonably and properly come within the scope of his contribution to the art.

I claim as my invention:

1. An injection system for use in a medical imaging examination, comprising:

a container containing a substance to be injected into a subject during a medical imaging examination, said substance in said container exhibiting a fill state;

a manually operated injector in fluid communication with said container, and adapted to interact with the subject to manually inject said substance from said container into said subject; and a detector arrangement that detects said fill state comprising a chamber separate from and in fluid communication with said container, said chamber, during injection of said substance into the subject, being temporarily occupied by a changing volume of said substance in said chamber, said volume being detectable and providing an indication of said fill state.

2. An injection system as claimed in claim 1 comprising a supply line placing said container and said chamber in fluid communication, and wherein said manually operated injector exerts pressure on said substance in said container to expel said substance from said container, and wherein said volume is a marking volume in said chamber having a magnitude dependent on said pressure.

3. An injection system as claimed in claim 2 wherein said chamber comprises a pressure-responsive membrane dividing said chamber into a first portion containing a gas, and a second portion containing said marking volume, with a relative proportion between said gas and said marking volume being detectable as said indication of said fill state.

4. An injection system as claimed in claim 3 wherein said chamber is disposed relative to an imaging device used to conduct said examination and wherein said chamber allows said proportion to be detectable by said device.

5. An injection system as claimed in claim 1 wherein said detector arrangement detects said fill state at a plurality of successive times between a beginning and an end of injection of said substance by said manually operated injector, and produces a time curve of said injection.

6. An injection system as claimed in claim 1 wherein said manually operated injector has a reservoir forming said container for said substance.

7. An injection system as claimed in claim 1 wherein said manually operated injector is a piston pump.

8. A medical examination system comprising:
   an image acquisition device adapted to interact with a subject to generate an image of an interior of the subject;
   a container containing a substance to be injected into the subject while said image is being generated by said image acquisition device, said substance having a fill state in said container;
   a manually-operated injector in fluid communication with said container and adapted for connection to the subject to deliver said substance from said container to the subject while said image is generated; and
   a chamber separate from and in fluid communication with said container, said chamber having a volume that is temporarily occupied by a changing volume said substance as said substance is delivered by said injector from said container to the subject, said container being disposed relative to said image acquisition device so as to be included in said image, and allowing detection of said volume of said substance in said chamber as an indication of said fill state of said substance in said container.

9. An medical examination system as claimed in claim 8 comprising a supply line proceeding between said injector and the subject, through which said substance is delivered from said injector to the subject, said chamber being connected in said supply line.

10. An medical examination system as claimed in claim 8 wherein said manually operated injector has a reservoir forming said container for said substance.

11. An medical examination system as claimed in claim 8 wherein said manually-operated injector exerts pressure on said substance to deliver said substance from said container to the subject, and wherein said chamber comprises a pressure-responsive membrane dividing said chamber into a first sub-chamber containing a gas, and a second sub-chamber containing said volume, as a marking volume, said marking volume deforming said membrane dependent on said pressure and thereby changing a proportion between said gas and said marking volume dependent on said fill state, and wherein said chamber allows detection of said proportion by said image acquisition device.

12. An medical examination system as claimed in claim 8 wherein said image acquisition device is a device selected from the group consisting of magnetic resonance tomography devices and computed tomography devices.

* * * * *